US009127307B2

(12) United States Patent
Adler, Jr. et al.

(10) Patent No.: US 9,127,307 B2
(45) Date of Patent: Sep. 8, 2015

(54) REAGENTS AND METHODS RELATING TO DNA ASSAYS USING AMPLICON PROBES ON ENCODED PARTICLES

(71) Applicant: PerkinElmer Health Sciences, Inc., Waltham, MA (US)

(72) Inventors: Karl Edwin Adler, Jr., Newburyport, MA (US); Mack J. Schermer, Belmont, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 13/773,089

(22) Filed: Feb. 21, 2013

(65) Prior Publication Data

US 2013/0157899 A1    Jun. 20, 2013

Related U.S. Application Data

(60) Division of application No. 13/052,795, filed on Mar. 21, 2011, now Pat. No. 8,404,463, which is a continuation of application No. 12/055,919, filed on Mar. 26, 2008, now Pat. No. 7,932,037.

(60) Provisional application No. 60/992,489, filed on Dec. 5, 2007.

(51) Int. Cl.
*C12P 19/34* (2006.01)
*C12Q 1/68* (2006.01)

(52) U.S. Cl.
CPC ............ *C12Q 1/6811* (2013.01); *C12Q 1/6809* (2013.01); *C12Q 1/6813* (2013.01); *C12Q 1/6876* (2013.01); *Y10T 436/143333* (2015.01)

(58) Field of Classification Search
CPC ........................... C12Q 1/6809; C12Q 1/6813
USPC ....................................................... 435/91.2
See application file for complete search history.

(56) References Cited

U.S. PATENT DOCUMENTS

| | | | |
|---|---|---|---|
| 4,310,408 A | 1/1982 | Rose et al. | |
| 4,499,052 A | 2/1985 | Fulwyler | |
| 5,028,545 A | 7/1991 | Soini | |
| 5,635,351 A | 6/1997 | Feuerstein et al. | |
| 5,670,314 A | 9/1997 | Christman et al. | |
| 5,830,645 A | 11/1998 | Pinkel et al. | |
| 5,926,387 A | 7/1999 | Furst | |
| 5,981,180 A | 11/1999 | Chandler et al. | |
| 6,048,695 A | 4/2000 | Bradley et al. | |
| 6,110,673 A | 8/2000 | Shayesteh et al. | |
| 6,268,147 B1 | 7/2001 | Beattie et al. | |
| 6,344,316 B1 | 2/2002 | Lockhart et al. | |
| 6,576,424 B2 | 6/2003 | Fodor et al. | |
| 6,916,621 B2 | 7/2005 | Shah | |
| 6,916,661 B2 | 7/2005 | Chandler et al. | |
| 7,106,513 B2 | 9/2006 | Moon et al. | |
| 7,164,533 B2 | 1/2007 | Moon et al. | |
| 2002/0028460 A1 | 3/2002 | Pinkel et al. | |
| 2002/0119455 A1 | 8/2002 | Chan | |
| 2004/0075907 A1 | 4/2004 | Moon et al. | |
| 2004/0125424 A1 | 7/2004 | Moon et al. | |
| 2004/0126875 A1 | 7/2004 | Putnam et al. | |
| 2004/0130761 A1 | 7/2004 | Moon et al. | |
| 2004/0130786 A1 | 7/2004 | Putnam et al. | |
| 2004/0132205 A1 | 7/2004 | Moon et al. | |
| 2004/0179267 A1 | 9/2004 | Moon et al. | |
| 2005/0260665 A1 | 11/2005 | Mohammed et al. | |
| 2006/0286570 A1 | 12/2006 | Rowlen et al. | |
| 2007/0009954 A1 | 1/2007 | Wang et al. | |
| 2007/0031829 A1 | 2/2007 | Yasuno et al. | |
| 2007/0042400 A1 | 2/2007 | Choi et al. | |
| 2007/0042419 A1 | 2/2007 | Barany et al. | |
| 2007/0166739 A1 | 7/2007 | Bobrow et al. | |
| 2007/0264636 A1* | 11/2007 | Crosby et al. ..................... 435/6 |
| 2010/0129875 A1* | 5/2010 | Schroeder ..................... 435/91.2 |
| 2011/0223602 A1* | 9/2011 | Whitman et al. ............ 435/6.11 |

FOREIGN PATENT DOCUMENTS

| | | |
|---|---|---|
| WO | WO-0055368 | 9/2000 |
| WO | WO-0186296 | 11/2001 |
| WO | WO-2004088310 | 10/2004 |
| WO | WO-2006072033 | 7/2006 |

(Continued)

OTHER PUBLICATIONS

Xu et al. Nucleic acids research, vol. 31, No. 8, e43, pp. 1-10.*
Fiegler, H. et al., DNA Microarrays for Comparative Genomic Hybridization Based on DOP-PCR Amplification of BAC and PAC Clones, *Genes, Chromosomes & Cancer*, 36: 361-374, 2003.
Chung, Y.J. et al., A Whole-Genome Mouse BAC Microarray with 1-Mb Resolution for Analysis of DNA Copy Number Changes by Array Comparative Genomic Hybridization, Genome Research, 14: 188-196, 2007.
Supplemental European Search Report for EP Application No. 08859169.8, dated Jan. 4, 2011.
Uda, A. et al., Comparison of Whole Genome Amplification Methods for Detecting Pathogenic Bacterial Genomic DNA Using Microarray, *Japanese Journal of Infectious Diseases*, 60: 355-361, 2007.
Telenius, H. et al., Degenerate Oligonucleotide-Primed PCR: General Amplification of Target DNA by a Single Degenerate Primer, *Genomics*, 13: 718-725, 1992.
Dutrillaux, B. et al., Characterization of Chromosomal Anomalies in Human Breast Cancer, *Cancer Genet. Cytogenet*., 49: 203-217, 1990.
Zhang, J. et al., Reconstruction of DNA sequencing by hybridization, *Bioinformatics*, 19: 14-21, 2003.

(Continued)

*Primary Examiner* — Cynthia B Wilder
(74) *Attorney, Agent, or Firm* — Gifford, Krass, Sprinkle, Anderson & Citkowski, P.C.

(57) ABSTRACT

Encoded bead multiplex assays for chromosomal gains and losses are provided that provide the benefits of complex, large template DNA sources, such as BAC DNA, as the probe material without bead networking or other assay performance problems. Reagents for assaying DNA are described herein which include a plurality of encoded particles having attached amplicons amplified from a template DNA sequence. Each individual attached amplicon includes a nucleic acid sequence identical to a random portion of the template DNA sequence, wherein the amplicons together represent substantially the entire template DNA and wherein the nucleic acid sequence identical to a random portion of the template DNA sequence of each individual amplicon is shorter than the entire template DNA.

4 Claims, 11 Drawing Sheets

(56) References Cited

FOREIGN PATENT DOCUMENTS

| WO | WO-2006105409 | 10/2006 |
| WO | WO-2007075894 A2 | 7/2007 |

OTHER PUBLICATIONS

Tsubosa, Y. et al., Effects of Degenerate Oligonucleotide-Ptrimed Polymerase Chain Reaction Amplification and Labeling Methods on the Sensitivity and Specificity of Metaphase- and Array-Based Comparative Genomic Hybridization, *Cancer Genetics and Cytogenetics*, 158(2): 156-166, Apr. 15, 2005.

Huang, Q. et al., Improving Degenerate Oligonucleotide Primed PCR-Comparative Genomic Hybridization for Analysis of DNA Copy Number Changes in Tumors, *Genes, Chromosomes & Cancer*, 28: 395-403, 2000.

Snijders, A.M. et al., Assembly of Microarrays for Genome-Wide Measurement of DNA Copy Number, Nature Genetics, Nature Publishing Group, vol. 29, No. 3, Nov. 1, 2001, pp. 263-264.

Jonsson, Goeran et al., High-Resolution Genomic Profiles of Breast Cancer Cell Lines Assessed by Tiling BAC Array Comparative Genomic Hybridization, *Genes Chromosomes & Cancer*, 46:6, 543-558, 2007.

Karhu, R., Four-Color CGH: A New Method for Quality Control of Comparative Genomic Hybridization, Genes, Chromosomes & Cancer, 24: 112-18, 1999.

Knijnenburg, J. et al., Rapid detection of genomic imbalances using micro-arrays consisting of pooled BACs covering all human chromosome arms, Nucleic Acids Research, 33(18): e159, 2005.

Pinkel, D. et al., Array comparative genomic hybridization and its applications in cancer, Nature Geneics, 37: 511-17, Jun. 2005.

Ross, M. et al., Selection of a human chromosome 21 enriched YAC sub-library using a chromosome-specific composite probe, Nature Genetics, 1: 284-90, Jul. 1992.

Snijders, A.M. et al., Assembly of Microarrays for Genome-Wide Measurement of DNA Copy Number, Nature Genetics, Nature Publishing Group, 29:3, 263-264, 2001.

\* cited by examiner

| | BAC* | Chromosome | BAC cyto band location | Bead ID |
|---|---|---|---|---|
| 1 | RP11-186J16 | 13 | 13q12.3 | 42 |
| 2 | RP11-186J16 | | 13q12.3 | 86 |
| 3 | RP11-117I13 | | 13q12.3 | 87 |
| 4 | RP11-480G1 | | 13q13.1 | 85 |
| 5 | RP11-189B4 | | 13q14.11 | 83 |
| 6 | RP11-174I10 | | 13q14.2 | 37 |
| 7 | RP11-142D16 | | 13q14.3 | 84 |
| 8 | RP11-138D23 | | 13q21.1 | 34 |
| 9 | RP11-411B10 | 18 | 18p11.21 | 88 |
| 10 | RP11-55N14 | | 18p11.31 | 57 |
| 11 | RP11-78H1 | | 18p11.32 | 90 |
| 12 | RP11-63N12 | | 18q12.1 | 45 |
| 13 | RP11-63N12 | | 18q12.1 | 89 |
| 14 | RP11-160B24 | | 18q21.2 | 36 |
| 15 | RP11-88B2 | | 18q22 | 51 |
| 16 | RP11-89N1 | | 18q23 | 48 |
| 17 | RP11-108H5 | 21 | 21q21.3 | 35 |
| 18 | RP11-147H1 | | 21q21.3 | 67 |
| 19 | RP11-17O20 | | 21q21.3 | 69 |
| 20 | RP11-17O20 | | 21q22.1 | 47 |
| 21 | RP11-79A12 | | 21q22.12 | 38 |
| 22 | RP11-190A24 | | 21q22.12 | 68 |
| 23 | RP11-88N2 | | 21q22.3 | 58 |
| 24 | GS-63-H24 | | 21q22.3 | 78 |
| 25 | RP11-46A10 | Autosomal & negative controls | 10q26.3) | 12 |
| 26 | RP11-35P20 | | 11p13 | 13 |
| 27 | RP11-122N11 | | 12p13.33 | 14 |
| 28 | RP11-462G8 | | 16p13.3 | 6 |
| 29 | RP11-698N11 | | 17p11.2 | 7 |
| 30 | RP11-598F7 | | 1q25.2 | 32 |
| 31 | RP11-568F1 | | 22q11.21 | 8 |
| 32 | RP11-416I2 | | 7q11.22 | 41 |
| 33 | RP11-319F4 | | 8p23.1 | 11 |
| | GTCACATGCGATGGATCGAGCTC (SEQ ID NO. 5) | | Negative Control Oligo | 29 |
| | CTTTATCATCGTTCCCACCTTAAT (SEQ ID NO. 6) | | Negative Control Oligo | 54 |
| | GCACGGACGAGGCCGGTATGTT (SEQ ID NO. 7) | | Negative Control Oligo | 56 |
| 34 | RP11-38O23 | X | Xp11.23 | 72 |
| 35 | RP11-495K15 | | Xp21.1-Xp21.1 | 73 |
| 36 | RP11-79B3 | | Xp22.11 | 74 |
| 37 | RP11-483M24 | | Xp22.31 | 75 |
| 38 | RP11-589J20 | | Xp22.31 | 76 |
| 39 | RP11-465E19 | | Xp11.1-Xp11.23 | 44 |
| 40 | RP11-292J24 | | Xp11.21 | 43 |
| 41 | RP11-258I23 | | Xp11.3-Xp11.4 | 63 |
| 42 | RP1-185L21 | | Xp22.22 | 66 |
| 43 | RP11-963J21 | | Xq27.3 | 65 |
| 44 | RP11-90N17 | | Xq11-Xq11 | 52 |
| 45 | RP3-368A4 | | Xq12-Xq12 | 53 |
| 46 | RP11-400O10 | Y | Yp11.31 | 20 |
| 47 | RP11-336F2 | | Yq11.223 | 77 |
| 48 | RP11-26D12 | | Yq11.23 | 17 |
| 49 | RP11-392F24 | | Yq11.222 | 18 |
| 50 | RP11-79J10 | | Yq11.23 | 19 |
| 51 | RP11-375P13 | | Yp11.2 | 64 |
| 52 | RP11-112L19 | | Yp11.31 | 33 |
| 53 | RP11-20H21 | | Yq11.22 | 61 |
| 54 | RP11-71M14 | | Yq11.221 | 46 |
| 55 | RP11-214M24 | | Yq11.23 | 62 |

*or negative control oligo

Figure 9

SEQUENCE LISTING

<160> NUMBER OF SEQ ID NOS: 7

<210> SEQ ID NO 1
<211> LENGTH: 22
<212> TYPE: DNA

```
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (11)..(16)
<223> OTHER INFORMATION: n is a, c, g, or t

<400> SEQUENCE: 1
ccgactcgag nnnnnnctag aa                                              22

<210> SEQ ID NO 2
<211> LENGTH: 22
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (11)..(16)
<223> OTHER INFORMATION: n is a, c, g, or t

<400> SEQUENCE: 2
ccgactcgag nnnnnntagg ag                                              22

<210> SEQ ID NO 3
<211> LENGTH: 22
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (11)..(16)
<223> OTHER INFORMATION: n is a, c, g, or t

<400> SEQUENCE: 3
ccgactcgag nnnnnnttct ag                                              22

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
ggaaacagcc cgactcgag                                                  19

<210> SEQ ID NO 5
<211> LENGTH: 23
<212> TYPE: DNA
<213> ORGANISM: Artificial Sequence
<220> FEATURE:
<223> OTHER INFORMATION: control oligonucleotide

<400> SEQUENCE: 5
gtcacatgcg atggatcgag ctc                                             23

<210> SEQ ID NO 6
<211> LENGTH: 24
<212> TYPE: DNA
<213> ORGANISM: Artificial Sequence
<220> FEATURE:
<223> OTHER INFORMATION: control oligonucleotide

<400> SEQUENCE: 6
ctttatcatc gttcccacct taat                                            24
```

```
<210> SEQ ID NO 7
<211> LENGTH: 22
<212> TYPE: DNA
<213> ORGANISM: Artificial Sequence
<220> FEATURE:
<223> OTHER INFORMATION: control oligonucleotide

<400> SEQUENCE: 7
gcacggacga ggccggtatg tt                                              22
```

REAGENTS AND METHODS RELATING TO DNA ASSAYS USING AMPLICON PROBES ON ENCODED PARTICLES

REFERENCE TO RELATED APPLICATIONS

This application is a divisional of U.S. patent application Ser. No. 13/052,795, filed Mar. 21, 2011, which is a continuation of U.S. patent application Ser. No. 12/055,919, filed Mar. 26, 2008, now U.S. Pat. No. 7,932,037, which claims priority to U.S. Provisional Patent Application Ser. No. 60/992,489, filed Dec. 5, 2007, the entire content of all of which is incorporated herein by reference.

FIELD OF THE INVENTION

Technology described herein relates generally to methods and compositions for detection of nucleic acids. More specifically described are methods and compositions for multiplex assays of genomic DNA.

BACKGROUND OF THE INVENTION

Assays for detection of genomic gain and loss allow for detection and diagnosis of genetic abnormalities which can underlie disease, behavioral and cognitive conditions, and other genetic-based pathologies. An encoded bead multiplex assay for chromosomal gains and losses is required that provides the benefits of BAC DNA as the probe material without bead networking or other assay performance problems.

SUMMARY OF THE INVENTION

A method of assaying a DNA sample including providing a first encoded particle set which itself includes encoded particles having attached amplicons. The amplicons contain random nucleic acid sequences which together represent substantially an entire first template DNA sequence. The amplicons of the first encoded particle set are hybridized with detectably labeled sample DNA and with detectably labeled reference DNA. A first signal is detected which is indicative of specific hybridization of the amplicons of the first encoded particle set with detectably labeled sample DNA. A second signal is detected which is indicative of specific hybridization of the amplicons of the first encoded particle set with detectably labeled reference DNA. The first and the second signals are compared to detect differences between the first and second signals and differences between the first and second signals is indicative of differences between the sample DNA and the reference DNA.

Optionally, the attached amplicons have a length in the range of about 500-1200 nucleotides, inclusive.

The detectably labeled sample DNA can be DNA obtained from an individual subject, such as genomic DNA. The subject is a human in particular embodiments of methods described herein.

Embodiments of methods described herein further include providing a second encoded particle set which includes encoded particles having attached amplicons. The amplicons of the second encoded particle set include DNA sequences which together represent substantially an entire second template DNA sequence. The amplicons of the second encoded particle set are hybridized with detectably labeled sample DNA and with detectably labeled reference DNA. A first signal is detected which is indicative of specific hybridization of the amplicons of the second encoded particle set with detectably labeled sample DNA. A second signal is detected which is indicative of specific hybridization of the amplicons of the second encoded particle set with detectably labeled reference DNA. The first and the second signals are compared to detect differences between the first and second signals and differences between the first and second signals is indicative of differences between the sample DNA and the reference DNA.

In particular embodiments, the first and second encoded particle sets are provided in a mixture. Embodiments of methods of using a mixture of encoded particle sets further include associating encoding of the individual particle sets with the signals detected so as to associate the signals relating to particular template DNA with differences between the sample DNA and the reference DNA.

Amplicons attached to each encoded particle set include random nucleic acid sequences which together represent substantially an entire template DNA sequence. In particular embodiments, the entire template DNA sequence is larger than each individual attached amplicon. In a particular example, the entire template DNA sequence has a length in the range of about 20-300 kilobases, inclusive and each individual attached amplicon includes a nucleic acid sequence identical to a portion of the template DNA sequence having a length in the range of about 500-1200 nucleotides, inclusive.

A method of preparing an encoded bead set for assaying DNA is described which includes a) performing a first amplification reaction using a DNA template and first reaction oligonucleotide primers. In this reaction, each of the plurality of first reaction primers includes a variable non-specific degenerate DNA sequence and a contiguous constant DNA sequence. A reaction product of this first reaction includes first amplicons, wherein each individual first amplicon includes a DNA sequence identical to a random portion of the DNA template and a DNA sequence identical to the constant DNA sequence of the first reaction primers. Further included in a method is b) performing a second amplification reaction using at least a portion of the first amplicons as template DNA and using second reaction oligonucleotide primers. The second reaction oligonucleotide primers include the constant DNA sequence of the first reaction primers and the second amplification reaction yields a second reaction product including second amplicons. Each individual second amplicon includes a DNA sequence identical to a random portion of the DNA template and a DNA sequence identical to the constant DNA sequence of the first reaction primers. Further included is c) binding the second amplicons to a first plurality of encoded particles thereby producing an encoded particle set for assaying DNA.

Optionally, the second reaction oligonucleotide primers further include a functional group for reaction with an encoded particle. For example, a 5' terminal amine can be included.

In further embodiments, a)-c) are repeated using a second DNA template and binding second amplicons obtained thereby to a second plurality of encoded particles which are detectably different than the first plurality of encoded particles. A second encoded particle set for assaying DNA is generated by this process. In still further embodiments, a)-c) are repeated using a third, fourth, fifth or subsequent genomic DNA template and binding the third, fourth, fifth or subsequent amplicons produced thereby to a third, fourth, fifth or subsequent plurality of encoded particles, each of the third, fourth, fifth or subsequent plurality of encoded particles detectably different than each other plurality of encoded particles, yielding a third, fourth, fifth or subsequent encoded particle set for assaying DNA. No limit on the number of encoded particle sets which can be generated using different DNA templates is intended to be described. Any number of encoded particle sets can be generated. Moreover, any suitable number of encoded particle sets can be mixed to produce a multiplex DNA assay reagent.

A reagent for assaying DNA is described herein which includes a plurality of encoded particles having attached amplicons amplified from a template DNA sequence. Each individual attached amplicon includes a DNA sequence identical to a random portion of the template DNA sequence, wherein the amplicons together represent substantially the entire template DNA and wherein the DNA sequence identical to a random portion of the template DNA sequence of each individual amplicon is shorter than the entire template DNA. For example, in specific embodiments, the entire template DNA sequence may have a length in the range of about 20-300 kilobases, inclusive and each individual attached amplicon each individual attached amplicon comprises a DNA sequence identical to a random portion of the template DNA sequence having a length in the range of about 500-1200 nucleotides, inclusive.

A multiplex reagent for assaying DNA is described herein which includes a mixture of two or more pluralities of particles encoded such that particles of each plurality of particles are detectably distinguishable from particles of each other plurality of particles. The encoded particles have attached amplicons amplified from a template DNA sequence, and each plurality of encoded particles has attached amplicons amplified from a different template DNA sequence compared to each other plurality of encoded particles. Further, each individual attached amplicon includes a DNA sequence identical to a random portion of the template DNA sequence.

A kit for assaying DNA is provided which includes an encoded particle set and/or a mixture of two or more encoded particle sets.

BRIEF DESCRIPTION OF THE DRAWINGS

FIG. 9 is a table displaying the BAC clones used to generate amplicons immobilized onto encoded beads in the example assays, their chromosome and cytoband locations, the sequence of the negative control oligonucleotide, and the bead ID (Luminex bead region) for the bead set to which each amplicon probe is immobilized.

DETAILED DESCRIPTION OF THE INVENTION

Methods and compositions relating to encoded particle multiplex assays for chromosomal gains and losses are provided herein.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004.

The term "nucleic acid" as used herein refers to RNA or DNA molecules having more than one nucleotide in any form including single-stranded, double-stranded, oligonucleotide or polynucleotide.

Reagent Compositions

A reagent for assaying genomic DNA is provided which includes a plurality of encoded particles having attached amplicons as probes. The amplicons attached to the plurality of encoded particles each include a nucleic acid sequence identical or completely complementary to a portion of a template genomic nucleic acid and together the amplicons represent substantially the entire template genomic nucleic acid.

Figure 1:
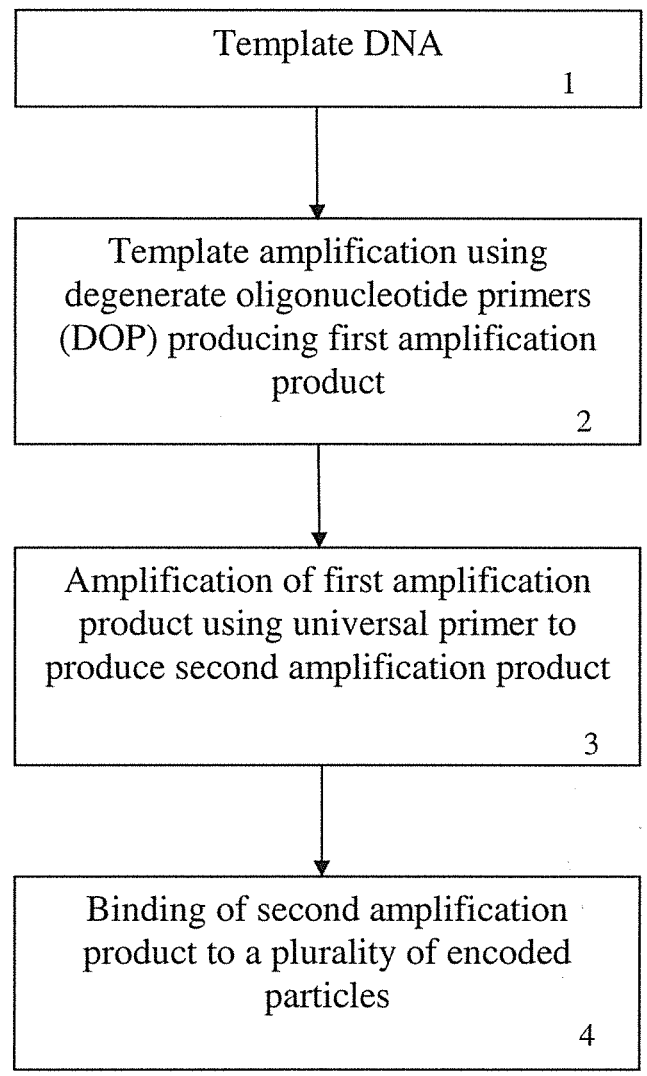
FIG. 1 is a flowchart illustrating an embodiment including preparing amplicons from template DNA using two amplification reactions and immobilizing the amplicons as probes onto a set of encoded beads, where the beads in the set all have the same ID code.

FIG. 1 illustrates an embodiment of a process for making a reagent for assaying genomic DNA. As indicated in FIG. 1, a template nucleic acid is provided, 1. The template is amplified, 2, in a first amplification reaction using degenerate oligonucleotide primers (DOP) to produce a first amplification product.

The template nucleic acid can be any nucleic acid capable of being copied using a nucleic acid amplification method.

The template DNA for this first amplification reaction is optionally genomic DNA, typically having a size in the range of about 20-300 kb, although the template can be smaller or larger. The term "genomic" refers to DNA of the genome of a cell or organism and includes DNA isolated directly from a cell or organism, such as microdissected chromosomal DNA, as well as DNA copied from DNA of the genome of a cell or organism, such as cloned DNA. The template DNA can encompass all or part of a genome of a cell or organism. The template DNA can encompass DNA representing one or more chromosomes, a portion of a chromosome, a genetic locus, a gene or a portion of a gene. The template DNA can be in any form, such as an insert in a vector illustratively including a bacterial artificial chromosome, yeast artificial chromosome, human artificial chromosome, cosmid, plasmid, phagemid, phage DNA or fosmid. Template DNA can be in the form of microdissected chromosomal DNA. Thus, while specific examples described herein refer to BACs as sources of template DNA, other types of clones such as PACs, YACs, cosmids, fosmids, cDNAs and the like may be used.

Template genomic DNA is obtained by methods known in the art, for instance, as described in J. Sambrook and D. W. Russell, Molecular Cloning: A Laboratory Manual, Cold Spring Harbor Laboratory Press; 3rd Ed., 2001 or F. M. Ausubel, Ed., Short Protocols in Molecular Biology, Current Protocols; 5th Ed., 2002. Template DNA may also be obtained commercially and/or using commercial kits for isolation of genomic DNA.

Amplification of template DNA is achieved using an in vitro amplification method. The term "amplification method" refers to a method or technique for copying a template nucleic acid, thereby producing nucleic acids including copies of all or a portion of the template nucleic acid, the produced nucleic acids also termed amplicons.

Amplicons optionally contain nucleic acid sequences present in the primers and not present in the original DNA template. Such primer-derived nucleic acids add functionality such as primer binding sites for additional amplification reactions and/or a functional group for chemical bonding to a substrate.

Amplification methods illustratively including PCR, ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

Many combinations of particular DNA template sources and nucleic acid amplification methods may be used.

The term "oligonucleotide primer" refers to a nucleic acid that is capable of acting as a site of initiation of synthesis of a primer extension product under appropriate reaction conditions. An oligonucleotide primer is typically about 10-30 contiguous nucleotides in length. An oligonucleotide primer is completely or substantially complementary to a region of a template nucleic acid such that, under hybridization conditions, the oligonucleotide primer anneals to the complementary region of the template nucleic acid. Appropriate reactions conditions for synthesis of a primer extension product include presence of suitable reaction components including, but not limited to, a polymerase and nucleotide triphosphates. Design of oligonucleotide primers suitable for use in amplification reactions is well known in the art, for instance as described in A. Yuryev et al., PCR Primer Design, Humana Press, 2007.

The term "degenerate oligonucleotide primer" refers to a primer which includes a nucleic acid having a random or semi-random nucleotide sequence. Design of degenerate oligonucleotide primers suitable for particular nucleic acid amplification reactions is well known in the art for instance as described in A. Yuryev et al., PCR Primer Design, Humana Press, 2007. Random or semi-random nucleotide sequences having about 5-8 nucleotides can be used. In further embodiments, random or semi-random nucleotide hexamers are included in degenerate oligonucleotide primers used in the first amplification.

The degenerate oligonucleotide primers used in particular embodiments each include a 5' constant DNA segment, an intermediate random DNA segment and a 3' anchor segment, for example as described in Fiegler et al., Genes Chromosomes Cancer, 36(4):361-74, 2003; and Telenius, et al., Genomics 13:718-25, 1992. The 5' constant DNA segment optionally has the same nucleotide sequence in all of the DOPs. The 3' anchor segment optionally has a nucleotide sequence determined to have a desired frequency of occurrence in the template nucleic acid. Analysis of frequency of occurrence of a particular nucleic acid sequence is well known in the art, for example, as described in Milosavljevic, A. and Jurka, J., 1993, Comput. Applic. Biosci., 9:407-411; Pesole, G. et al., 1992, Nucleic Acids, Res., 20:2871-2875; and Hutchinson, G. B., 1996, Comput. Appl. Biosci., 12:391-398.

In particular embodiments the DOPs include about 17-25 contiguous nucleotides, of which about 7-12 contiguous nucleotides are included in the 5' constant DNA segment, about 5-8 contiguous nucleotides are included in the random DNA segment and about 5-8 contiguous nucleotides are included in the 3' anchor segment.

The first amplification reaction yields a first reaction product containing a plurality of amplicons. Each individual amplicon in the first reaction product includes a DNA sequence identical or completely complementary to a random portion of the DNA template and a DNA sequence identical to the 5' constant DNA sequence of the first reaction primers.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100%, or completely, complementary to a region of the nucleotide sequence 5'-TTAGCTGG-3'.

Referring to FIG. 1, a second amplification reaction, 3, is performed using the first reaction product amplicons as template DNA. The second amplification reaction, 3, includes a "universal" oligonucleotide primer, so-called since the universal primer is identical or completely complementary to the 5' constant DNA segment of the DOP used in the first amplification reaction. A universal oligonucleotide primer includes the 5' constant DNA segment of the DOP used in the first amplification reaction positioned at the 3' end of the universal primer. A universal oligonucleotide primer optionally includes additional contiguous nucleotides at the 5' end of the primer.

In a particular option, a universal oligonucleotide primer includes a functional group at the 5' terminus of the primer for attachment of the amplicons resulting from the second amplification reaction to an encoded solid or semi-solid substrate such as encoded particles. For example, the universal oligonucleotide primers include an amine group at the 5' terminus of the primer. In a further option, amplicons resulting from the second amplification reaction can be modified to include a functional group for bonding to a solid or semi-solid substrate Modification of a nucleic acid to include a functional group capable of bonding to a solid or semi-solid substrate is well known in the art.

In particular embodiments, each individual amplicon attached to a particle includes a DNA segment identical to a random portion of the template DNA sequence. Each individual amplicon also contains a constant DNA segment contiguous with the DNA segment identical to a random portion of the template DNA sequence. The constant DNA segment of the amplicon optionally includes a terminal functional group for attachment of the amplicon to an encoded particle.

In a particular embodiment, the constant DNA segment of the amplicon includes a 5' terminal amine group for attachment of the amplicon to an encoded particle.

As shown in FIG. 1, the amplicons of the second reaction product are immobilized, 4, on a first plurality of encoded particles. Binding of the amplicons of the second amplification reaction to the encoded particles is achieved by any of various methods effective to bond a nucleic acid to a solid or semi-solid substrate, illustratively including adsorption and chemical bonding. The amplicons can be bonded directly to the material of the encoded particles or indirectly bonded to the encoded particles, for example, via bonding to a coating or linker disposed on the particles. Amplicons can be synthesized, and/or modified once synthesized, to include a functional group for use in bonding the amplicons to particles. For example, amplicons can include carboxyl, amine, amino, carboxylate, halide, ester, alcohol, carbamide, aldehyde, chloromethyl, sulfur oxide, nitrogen oxide, epoxy and/or tosyl functional groups.

Particles to which amplicons are bound can be any solid or semi-solid particles to which amplicons can be attached, which are suitable for a multiplex assay and which are stable and insoluble under hybridization and detection conditions. The particles can be of any shape, such as cylindrical, spherical, and so forth, size, composition, or physiochemical characteristics. The particle size or composition can be chosen so that the particle can be separated from fluid, e.g., on a filter with a particular pore size or by some other physical property, e.g., a magnetic property.

Microparticles, such as microbeads, used can have a diameter of less than one millimeter, for example, a size ranging from about 0.1 to about 1,000 micrometers in diameter, inclusive, such as about 3-25 microns in diameter, inclusive, or about 5-10 microns in diameter, inclusive. Nanoparticles, such as nanobeads used can have a diameter from about 1 nanometer (nm) to about 100,000 nm in diameter, inclusive, for example, a size ranging from about 10-1,000 nm, inclusive, or for example, a size ranging from 200-500 nm, inclusive. In certain embodiments, particles used are beads, particularly microbeads and nanobeads.

Particles are illustratively organic or inorganic particles, such as glass or metal and can be particles of a synthetic or naturally occurring polymer, such as polystyrene, polycarbonate, silicon, nylon, cellulose, agarose, dextran, and polyacrylamide. Particles are latex beads in particular embodiments.

Particles used include functional groups for binding to amplicons in particular embodiments. For example, particles can include carboxyl, amine, amino, carboxylate, halide, ester, alcohol, carbamide, aldehyde, chloromethyl, sulfur oxide, nitrogen oxide, epoxy and/or tosyl functional groups. Functional groups of particles, modification thereof and binding of a chemical moiety, such as a nucleic acid, thereto are known in the art, for example as described in Fitch, R. M., Polymer Colloids: A Comprehensive Introduction, Academic Press, 1997. U.S. Pat. No. 6,048,695 describes an exemplary method for attaching nucleic acid probes, such as amplicons, to a substrate, such as particles. In a further particular example, 1-Ethyl-3-[3-dimethylaminopropyl]carbodiimide hydrochloride, EDC or EDAC chemistry, can be used to attach amplicons to encoded particles.

Encoded particles are particles which are distinguishable from other particles based on a characteristic illustratively including an optical property such as color, reflective index and/or an imprinted or otherwise optically detectable pattern. For example, the particles may be encoded using optical, chemical, physical, or electronic tags. Encoded particles can contain or be attached to, one or more fluorophores which are distinguishable, for instance, by excitation and/or emission wavelength, emission intensity, excited state lifetime or a combination of these or other optical characteristics. Optical bar codes can be used to encode particles.

In particular embodiments, each particle of a particle set is encoded with the same code such that each particle of a particle set is distinguishable from each particle of another particle set. In further embodiments, two or more codes can be used for a single particle set. Each particle can include a unique code, for example. In certain embodiments, particle encoding includes a code other than or in addition to, association of a particle and a nucleic acid probe specific for genomic DNA.

In particular embodiments, the code is embedded, for example, within the interior of the particle, or otherwise attached to the particle in a manner that is stable through hybridization and analysis. The code can be provided by any detectable means, such as by holographic encoding, by a fluorescence property, color, shape, size, light emission, quantum dot emission and the like to identify particle and thus the capture probes immobilized thereto. In some embodiments, the code is other than one provided by a nucleic acid.

One exemplary platform utilizes mixtures of fluorescent dyes impregnated into polymer particles as the means to identify each member of a particle set to which a specific capture probe has been immobilized. Another exemplary platform uses holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Patent Application Publications 20040179267, 20040132205, 20040130786, 20040130761, 20040126875, 20040125424, and 20040075907 describe exemplary particles encoded by holographic barcodes. U.S. Pat. No. 6,916,661 describes polymeric microparticles that are associated with nanoparticles that have dyes that provide a code for the particles While an embodiment described in detail herein utilizes the Luminex encoded bead platform, other types of encoded particle assay platforms may be used, such as the VeraCode beads and BeadXpress system (Illumina Inc., San Diego Calif.), xMAP 3D (Luminex) and the like. Magnetic Luminex beads can be used which allow wash steps to be performed with plate magnets and pipetting rather than with filter plates and a vacuum manifold. Each of these platforms are typically provided as carboxyl beads but may also be configured to include a different coupling chemistry, such as amino-silane.

In general, the amplicons which are the product of the second amplification reaction are double stranded and the double stranded amplicons are attached to the particles. Thus, both strands of the double stranded amplicons are represented on each particle. The amplicons are denatured and rendered single stranded after immobilization to the particles for preparation for use in particular embodiments of assay methods. Optionally, double stranded amplicons are denatured prior to immobilization and the single stranded amplicons are then bound to particles.

As described, each individual amplicon of both the first and second amplification reactions contains a nucleic acid sequence identical to a random portion of the template DNA sequence such that the amplicons produced by the first amplification reaction together represent substantially the entire template DNA sequence and the amplicons produced by the second amplification reaction together represent substantially the entire template DNA sequence.

Encoded particles having bound amplicons which are the product of a second amplification reaction and which together represent substantially the entire genomic DNA sequence used as a template in the first amplification reaction are a first particle set and a first reagent for assaying genomic DNA.

In particular embodiments, each individual amplicon attached to a particle has a length in the range of about 500-1200 nucleotides, inclusive. Thus, a relatively large template nucleic acid is represented substantially entirely on a set of encoded particles by the attached relatively smaller amplicons amplified from the template.

As noted above, each particle set includes encoded particles having bound amplicons which are the product of a second amplification reaction and which together represent substantially the entire genomic DNA sequence used as a template in a first amplification reaction. The number of particles including amplicons which is sufficient to together represent substantially the entire genomic DNA sequence used as a template in the first amplification reaction depends on a number of factors such as the size of the template, the size of the amplicons and the number of binding sites available for binding an amplicon on a particle. In general, the number of particles sufficient to together represent substantially the entire genomic DNA sequence used as a template in the first amplification reaction is in the range of about 1-10,000, inclusive.

Additional particle sets are generated by amplification using a second genomic DNA template and binding the amplicons which are the reaction product of a second amplification reaction as described above to a second plurality of encoded particles. The second plurality of encoded particles is detectably different than the first plurality of encoded particles, thereby generating a second encoded particle set and a second reagent for assaying genomic DNA.

Similarly, a third or subsequent genomic DNA template is used to generate the reaction product of an amplification reaction and the reaction product is bound to a third or subsequent plurality of encoded particles. Each of the third or subsequent plurality of encoded particles is detectably different than each other plurality of encoded particles, yielding a third or subsequent encoded particle set and a third or subsequent reagent for assaying genomic DNA.

Multiplex Reagent

A multiplex reagent for assaying genomic DNA is provided according to certain embodiments which includes a mixture of two or more particle sets. The individual encoded particles of each encoded particle set are detectably distinguishable from individual encoded particles of each other encoded particle set in particular embodiments. Each encoded particle set has attached amplicons which are the product of a second amplification reaction as described herein and which together represent substantially the entire genomic DNA sequence used as a template in a first amplification reaction, wherein a different genomic template is represented by amplicons attached to each other encoded particle set.

A multiplex reagent according to a specific embodiment includes a first encoded particle set having attached amplicons which together represent substantially an entire template DNA sequence inserted in the first bacterial artificial chromosome and a second encoded particle set having attached amplicons which together represent substantially an entire template DNA sequence inserted in the second bacterial artificial chromosome.

For example, a first encoded particle set has attached amplicons including nucleic acid sequences identical to a portion of human chromosome 13 DNA and a second encoded particle set has attached amplicons including nucleic acid sequences identical to a portion of chromosome 18 human DNA. Third or subsequent encoded particle set have attached amplicons including nucleic acid sequences identical to human DNA from another chromosome or another non-overlapping region of a chromosome.

A multiplex reagent described herein allows for simultaneous assay of multiple targets, such as multiple genomic loci, in a single assay.

A multiplex reagent for assaying genomic DNA is generated by mixing at least a first encoded particle set and a second encoded particle set.

Figure 2:
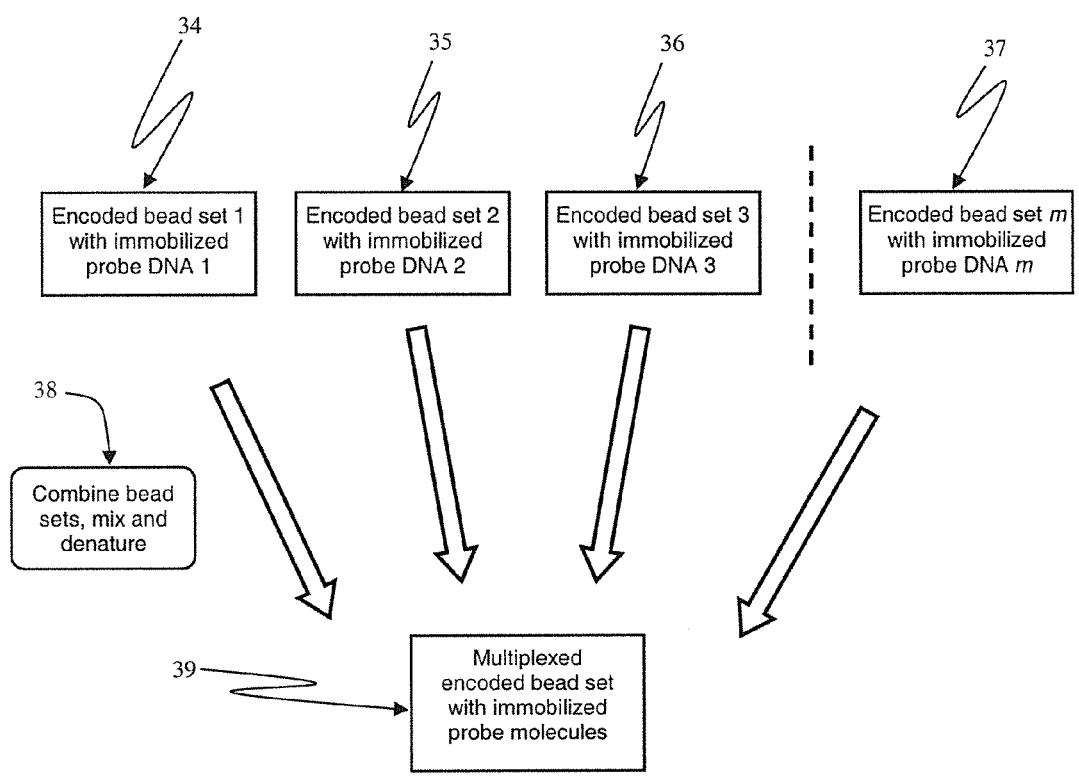
FIG. 2 is a flowchart illustrating an embodiment including mixing m different encoded bead sets, each with its respective immobilized BAC-amplicon probe DNA, together to make a multiplexed encoded bead set.

FIG. 2 illustrates an embodiment of a method of generating a multiplex reagent. As indicated in the figure, any number, "m" of encoded particle sets can be included in the multiplex reagent. Thus, for example, "m" can be at least 2, 3, 4, 5, 10, 15, 20, 25, 30, 35, 40, 45, 50, 55, 60, 65, 70, 75, 80, 85, 90, 95, 100 or 200 different encoded particle sets. A set of encoded particles having bound amplicons is combined with one or more additional sets of encoded particles having bound amplicons to generate a multiplex reagent for assay of genomic gain and loss in a sample.

Assay Methods

A method of assaying genomic DNA includes providing encoded particles having attached amplicons which together represent substantially an entire template genomic nucleic acid. In particular embodiments, encoded particles having attached amplicons are provided which together represent more than one copy of substantially an entire template genomic nucleic acid.

A sample of genomic DNA to be assayed for genomic gain and/or loss is labeled with a detectable label. Reference DNA is also labeled with a detectable label for comparison to the sample DNA. The sample and reference DNA can be labeled with the same or different detectable labels depending on the assay configuration used. For example, sample and reference DNA labeled with different detectable labels can be used together in the same container for hybridization with amplicons attached to encoded particles in particular embodiments. In further embodiments, sample and reference DNA labeled with the same detectable labels can be used in separate containers for hybridization with amplicons attached to particles.

The term "detectable label" refers to any atom or moiety that can provide a detectable signal and which can be attached to a nucleic acid. Examples of such detectable labels include fluorescent moieties, chemiluminescent moieties, bioluminescent moieties, ligands, magnetic particles, enzymes, enzyme substrates, radioisotopes and chromophores.

Any of various methods of labeling sample and reference DNA may be used in the assay, such as nick translation or chemical labeling of the DNA. For example, a detectable label can be introduced by polymerization using nucleotides that include at least some modified nucleotides, such as nucleotides modified to include biotin, digoxygenin, fluorescein, or cyanine. In some embodiments, the detectable label is introduced by random-priming and polymerization. Other examples include nick translation (Roche Applied Science, Indianapolis Ind.; Invitrogen, Carlsbad Calif.) and chemical labeling (Kreatech ULS, Amsterdam NL). Detectable labeling of nucleic acids is well known in the art and any labeling method appropriate for labeling genomic DNA can be used.

In yet another embodiment, covalent labeling of sample and reference DNA individually with a detectable label is avoided. For example, unlabeled genomic DNA samples are hybridized to the amplicons immobilized to the encoded particles. Pre-labeled reporter sequences are also hybridized to the amplicon-sample DNA complexes and amplicon-reference DNA complexes at sequences adjacent to but not overlapping the sequences of the capture probes of the amplicons. These labeled reporter sequences can be hybridized in the same or in a different hybridization reaction. In this manner the labeled reporter sequences can be manufactured in bulk in a larger-scale environment, lowering the cost per assay compared to individually labeling each sample at the time of the assay.

The "sample" and "reference" genomic DNA can be obtained from any suitable source. Particular methods described herein involve using sample genomic DNA from an individual subject. Genomic sample and/or reference DNA can be extracted from almost any tissue including, but not limited to, blood, amniotic fluid, solid tumors, organ biopsies, cheek swabs, chorionic villae, blastocysts and blastomeres, products of conception, saliva, urine and the like. Archived samples extracted from formalin-fixed, paraffin-embedded (FFPE) pathology samples are also sources of sample genomic DNA assayed by this method. Sample and/or reference genomic DNA can also be obtained from in vitro sources such as cell lines. Methods of obtaining genomic DNA from these or other sources are well known in the art.

In particular embodiments, reference DNA is characterized with respect to a particular characteristic of the sample DNA to be assayed. For example, where sample DNA is to be assayed to detect duplication of a particular gene or chromosomal locus, the reference DNA is characterized so that it is known how many copies of the gene or locus are contained in the reference DNA. In general, sample and reference DNA from the same species are used.

An assay described herein can be used to detect or characterize disorders associated with chromosomal gains or losses. Constitutional, or inborn, disorders include trisomies of entire chromosomes, amplifications or deletions of smaller genomic loci (approximately 200 kilobases to 20 megabases), and amplifications or deletions in the sub-telomeric or centromeric regions. Various cancers are also characterized by chromosomal gains and losses that may correlate with type, stage, drug resistance, or therapy response. Laboratory cell lines, including stem-cell lines, may be characterized for chromosomal stability using the present method.

While methods and compositions are described herein primarily with reference to nucleic acids derived from humans, it is appreciated that methods and compositions described herein may be used to assay sample genomic DNA from any of various organisms including, but not limited to, non-human primates, rodents, rabbits, dogs, cats, horses, cattle, pigs, goats and sheep. Non-mammalian sources of sample DNA can also be assayed, illustratively including fish and other aquatic organisms, birds, poultry, bacteria, viruses, plants, insects, reptiles, amphibians, fungi and mycobacteria.

The amplicons attached to the encoded particles are hybridized with detectably labeled sample genomic DNA of an individual subject so as to achieve specific hybridization of the amplicon DNA and the detectably labeled sample genomic DNA. In addition, DNA sequences attached to the encoded particles are hybridized with detectably labeled reference genomic DNA so as to achieve specific hybridization of the amplicon DNA and the detectably labeled reference genomic DNA.

The terms "hybridization" and "hybridized" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize. The terms "specific hybridization" and "specifically hybridizes" refer to hybridization of a particular nucleic acid to a target nucleic acid without substantial hybridization to nucleic acids other than the target nucleic acid in a sample.

Assays described can be performed in any suitable container. In particular embodiments, for example, where multiple samples are to be assayed, a multi-chamber container can be used. Multi-chamber containers illustratively include multi-depression substrates such as slides, silicon chips or trays. In some embodiments, each sample is disposed in a different well of a multi-well plate. For example, a multi-well plate can be a 96-well, 384-well, or 1024-well assay plate.

Further included is detection of a first signal indicating specific hybridization of the attached DNA sequences with detectably labeled genomic DNA of an individual subject and detection of a second signal indicating specific hybridization of the attached DNA sequences with detectably labeled reference genomic DNA.

Any appropriate method, illustratively including spectroscopic, optical, photochemical, biochemical, enzymatic, electrical and/or immunochemical is used to detect the detectable labels of the sample and reference DNA hybridized to amplicons bound to the encoded particles.

Signals that are indicative of the extent of hybridization can be detected, for each particle, by evaluating signal from one or more detectable labels. Particles are typically evaluated individually. For example, the particles can be passed through a flow cytometer. Exemplary flow cytometers include the Coulter Elite-ESP flow cytometer, or FACScan™ flow cytometer available from Beckman Coulter, Inc. (Fullerton Calif.) and the MOFLO™ flow cytometer available from Cytomation, Inc., Fort Collins, Colo. In addition to flow cytometry, a centrifuge may be used as the instrument to separate and classify the particles. A suitable system is that described in U.S. Pat. No. 5,926,387. In addition to flow cytometry and centrifugation, a free-flow electrophoresis apparatus may be used as the instrument to separate and classify the particles. A suitable system is that described in U.S. Pat. No. 4,310,408. The particles may also be placed on a surface and scanned or imaged.

A first signal is detected indicating specific hybridization of the encoded particle attached DNA sequences with detectably labeled genomic DNA of an individual subject. A second signal is also detected indicating specific hybridization of the encoded particle attached DNA sequences with detectably labeled reference genomic DNA.

The first signal and the second signal are compared, yielding information about the genomic DNA of the individual subject compared to the reference genomic DNA.

In particular embodiments, a ratio of the signals from the detectable labels of the reference DNA and the sample DNA hybridized to the amplicons of one or more particle sets is used to evaluate differences between the sample and reference DNA, indicative, for instance, of genomic gain and/or loss. In certain embodiments, the reference DNA and the sample DNA are hybridized to the amplicons of one or more particle sets in the same container, such as a well of a multi-well plate. After hybridization, the two labels are analysed together, i.e. both detectable labels are detected in the hybridized material or the hybridized material is divided into two (or more) portions and each portion is evaluated separately to detect the detectable labels. Results from the evaluation can be used to provide the ratio of signals from the two detectable labels. This approach allows use of competitive hybridization to normalize any variation between assays: both of the reference and experimental samples are assayed simultaneously in the same vessel mixed with the same particles.

Optionally, the detectably labeled reference DNA and the detectably labeled sample DNA are hybridized to one or more particle sets in the different containers, such as different wells of a multi-well plate. A ratio of signals from the two detectable labels can be obtained to evaluate differences between the sample DNA and reference DNA. When this approach is utilized, a single reference sample can be shared between several or many experimental samples. For experiments involving multiple samples per day there can be a savings on reagent cost and labor by avoiding the labeling of multiple duplicate normal samples. Also it is unnecessary to manipulate the sample to obtain different portions for separate analysis. Each sample can be evaluated only once.

Encoded particles are identified by their encoded information so as to associate particle encoding with the first signal and with the second signal in particular embodiments. Thus, for example, first and second signals are associated with encoded particles of a first encoded particle set containing human DNA from chromosome 13. The first signal and the second signal associated with the first encoded particle set are compared, yielding information about the chromosome 13 DNA of the individual subject compared to the chromosome 13 reference DNA. Similarly, first and second signals are associated with a second encoded particle set containing human DNA from chromosome 18. The first signal and the second signal associated with the second encoded particle set are compared, yielding information about the chromosome 18 DNA of the individual subject compared to the chromosome 18 reference DNA.

The figures and descriptions herein illustrate the best mode but many alternative materials and processes can be substituted. One of skill in the art will recognize appropriate alternative materials and processes and will be able to make and use the compositions and methods described without undue experimentation.

The compositions of the various buffers and other assay components may be substituted.

The conditions for culturing, purification amplification, denaturation, coupling, hybridization, reporter binding, washing, and bead handling can all be varied by the user to suit particular types of cells, template genomic DNA, samples, selected reporters and the like.

The assay in examples herein performs well with as little as 30 ng of sample DNA. In situations where the biological source yields insufficient DNA for the described assay the sample can be amplified by a variety of whole-genome amplification (WGA) methods, such as DOP PCR or phi-29 PCR. When utilizing WGA-processed samples, the reference DNA can be processed by the same method so that any sequence-specific amplification bias will be largely corrected by the sample/reference ratio of signals.

Kits for assaying DNA are provided. In particular embodiments, a kit is provided which includes an encoded particle set and/or a mixture of two or more encoded particle sets. Instructional material for use of the encoded particle set and/or multiplex reagent including two or more encoded particle sets is optionally included in a kit. An ancillary reagent such as buffers, enzymes, washing solutions, hybridization solutions, detectable labels, detection reagents and the like are also optionally included.

Embodiments of assay compositions and methods are illustrated in the following examples. These examples are provided for illustrative purposes and are not considered limitations on the scope of compositions and methods.

EXAMPLES

Example 1

Preparation of a Bead Set Reagent for Genomic DNA Assay

Figure 1A:
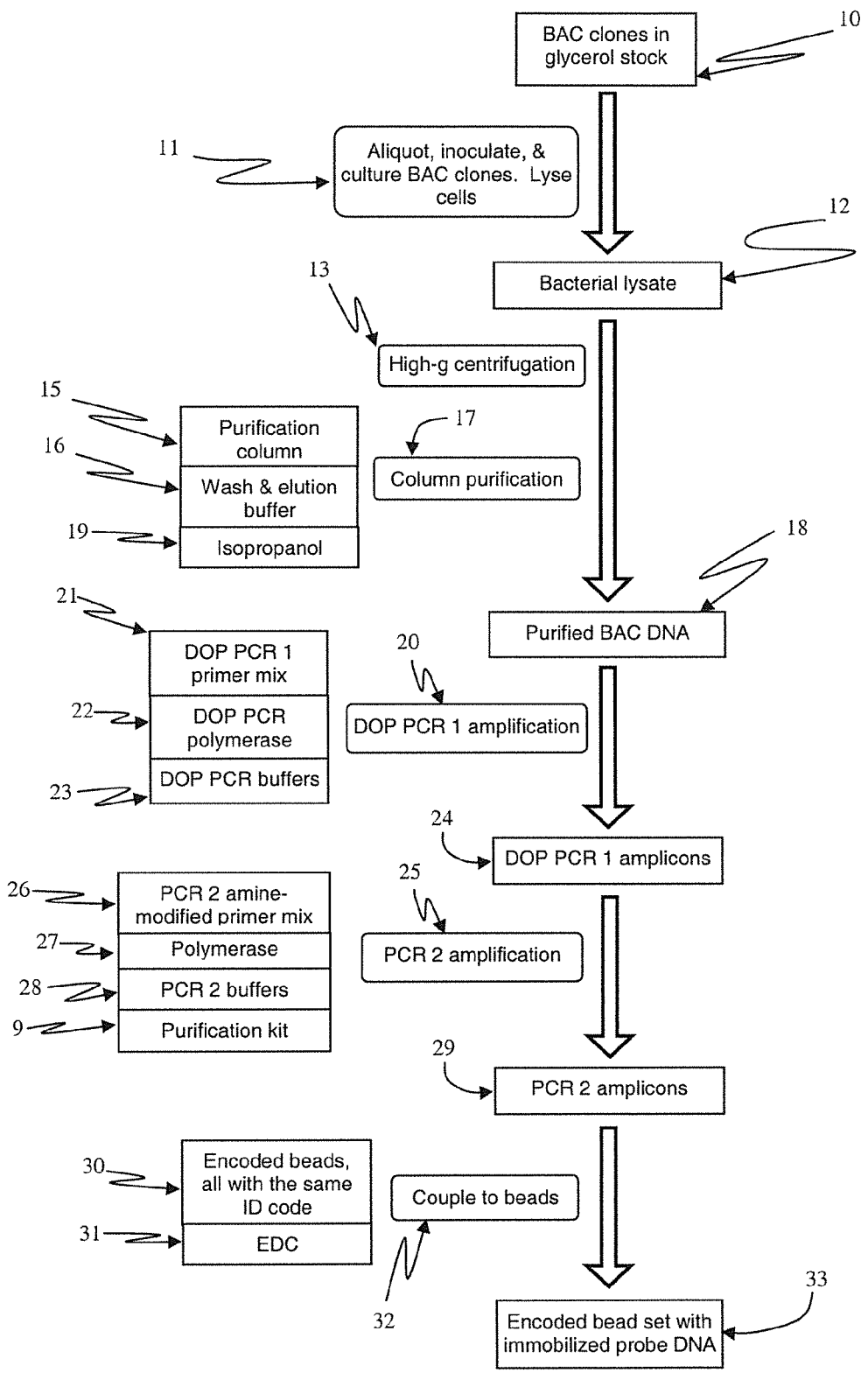
FIG. 1A is a flowchart illustrating an embodiment including preparing BAC amplicons from a single BAC clone and immobilizing the amplicons as probes onto a set of encoded beads, generating a bead set where the beads in the set all have the same ID code.

FIG. 1A shows a flowchart illustrating preparation of BAC amplicons from a single BAC clone and immobilizing the amplicons as probes onto a set of encoded beads. In this example, the beads in the set all have the same ID code.

The starting material is living BAC clone material, 10, a long (100-200 kilobases typically) human DNA sequence inserted into the genome of an *E. coli* bacteria cell. A small chip of frozen BAC glycerol stock material is picked and used as the starting material for a standard bacterial cell culture process, 11. The cells are cultured in 35 ml medium in 50 ml tubes overnight at 37° C. with a selective antibiotic according to a standard BAC culture protocol. The cultured cells are then centrifuged to the bottom of the tube at 4° C. for 20 minutes and the supernatant withdrawn and discarded. The cell pellet is resuspended in a buffer containing RNase, and then lysed using LyseBlue (Qiagen, Valencia Calif.) and SDS. The lysate, 12, is centrifuged, 13, at approximately 20,000 g for 30 minutes, and the supernatant, containing the DNA in solution, is collected and the pellet discarded. The centrifugation is repeated for 15 minutes on the supernatant. The clear supernatant containing the dissolved BAC DNA is collected, while the cellular debris, proteins and other impurities are driven to the bottom of the tube and discarded. The BAC DNA is extracted and purified, 17, from the supernatant using a Qiagen Genomic-Tip 20/G column purification kit. This kit comprises purification columns, 15, and wash and elution buffers, 16. After elution, the now highly purified BAC DNA is precipitated and into pellets by isopropanol, 19, precipitation. The yield is typically 20 to 200 ng of purified BAC DNA, 18. This BAC DNA can be stored as a dried pellet or resuspended in water for use immediately in the next steps.

A quantity of PCR amplicons representing substantially the entire sequence content of each BAC DNA is then produced using two rounds of polymerase chain reaction (PCR) amplification. The first round of PCR, 20, is non-specific degenerate oligonucleotide primer (DOP) PCR using a DOP primer mix, 21, a DOP PCR polymerase, 22, and DOP PCR buffer, 23, with the above prepared BAC DNA, 18, used as template. The second round of PCR amplification, 25, utilized a single primer directed at the known sequence motifs of the DOP primers. Two rounds of PCR are used to generate yields of approximately 20 µg of final amplicon product, 29, for subsequently coupling, 32, the amplicons, 29, to encoded beads, 30.

The amplicons are prepared as follows.
A first 50 µl DOP PCR mix is made for each BAC DNA comprised of:

| | |
|---|---|
| 10X DOP PCR Buffer | 5.0 µl |
| 10 mM dNTP's (each) | 1.0 µl |
| 50 mM MgCl | 5.0 µl |
| 10 uM DOP Primer Mix (each) | 10.0 µl |
| 20 to 50 ng BAC DNA Template | 2.0 µl |
| Platinum Taq polymerase | 0.5 µl |
| Water | 21.5 µl |
| Total Volume | 50.0 µl |

The DOP PCR buffer, 23, included 20 mM Tris HCL (pH 8.4), 50 mM KCl and 5 mM MgCl. The dNTPs (Amersham Biosciences, Piscataway N.J.) are at a concentration of 200 µM. The platinum TAQ polymerase (Applied BioSystems) is at a concentration of 5 units/µl. The DOP primer mix, 21, see Fiegler et al. 2003, Genes Chromosomes Cancer, 36(4):361-74, included three sets of degenerate oligonucleotides of the following 22-mer sequences (Operon Biotechnologies, Huntsville Ala.), wherein the Ns represent randomized nucleotides:

```
                                          SEQ ID NO. 1
5' CCGACTCGAGNNNNNNCTAGAA 3'

SEQ ID NO. 2
5' CCGACTCGAGNNNNNNTAGGAG 3'

SEQ ID NO. 3
5' CCGACTCGAGNNNNNNTTCTAG 3'
``` wherein N denotes random nucleotides.

The BAC DNA template, 18, dissolved in water, is purified by column purification, 17, using Qiagen Genomic-Tip 20/G column purification kit. The Platinum Taq polymerase, 22 (Invitrogen, Carlsbad Calif.) is at a concentration of 5 units/µl.

The first-round amplification, 20, is performed in a Gene-Amp 9700 themocycler (Applied BioSystems, Foster City Calif.) according to the following temperature/time profile:

| | | |
|---|---|---|
| 3.0 min | 94° C. | |
| 1.5 min | 94° C. | |
| 2.5 min | 30° C. | 9 Cycles |
| 0.10 C/sec | 72° C. (ramp) | |
| 3.0 min | 72° C. | |
| 1.0 min | 94° C. | |
| 1.5 min | 62° C. | 30 Cycles |
| 2.0 min | 72° C. | |
| 8.0 min | 72° C. | |
| 4.0° C. | | (steady state) |

The amplicon products, 24, from this first round of DOP PCR, 20, are then used as the templates for a second round of PCR, 25. The single primer, 26, in the second round is specific to the common sequence portions of the DOP primers, 21 used in the first round, 20. This primer, 26, is amine-modified so that the resulting amplicons, 29, would also have an amine group on one end to facilitate simple coupling to the encoded beads in a subsequent step, 32.

The second round PCR is performed as follows.
A second 100 µl PCR mix is made for each BAC amplicon template including:

| | |
|---|---|
| 10X PCR Buffer | 10.0 µl |
| 10 mM dNTP's (each) | 2.0 µl |
| 50 mM MgCl | 10.0 µl |
| 10 uM Amine Primer | 15.0 µl |
| Template (from PCR #1) | 2.0 µl |
| Platinum Taq | 0.5 µl |
| Water | 58.5 µl |
| Total Volume | 100.0 µl |

The PCR 2 buffer, 28, included 20 mM Tris HCL (pH 8.4), 50 mM KCl and 5 mM MgCl. The dNTPs (Amersham Biosciences, Piscataway N.J.) are at a concentration of 200 µM. The platinum TAQ polymerase (Applied BioSystems) is at a concentration of 5 units/µl.

The amine-linked primer (Operon) had the following sequence.

```
                                          SEQ ID NO. 4
5'-NH2-GGAAACAGCCCGACTCGAG-3'
```

The templates in reaction, 25, are the DOP amplicons, 24, from the previous DOP PCR round, 20. The second-round amplification, 25, is performed in a GeneAmp 9700 themocycler (Applied BioSystems) according to the following temperature/time profile:

| | | |
|---|---|---|
| 10 min | 95° C. | |
| 1.0 min | 95° C. | |
| 1.5 min | 60° C. | 35 Cycles |
| 7.0 min | 72° C. | |
| 10 min | 72° C. | |
| 4.0° C. | | (steady state) |

This second PCR product, 29, is then purified using a magnetic-bead based kit, 9, (PCR Clean Beads, Agencourt Bioscience Corp., Beverley Mass.) according to the manufacturer's protocol. The purified amplicons, 29, are then resuspended in 40 µl water and stored at −20° C. until used in the bead coupling step as described below.

The encoded bead coupling process, 32, to immobilize the amplicon product, 29, as probe DNA onto the surface of encoded beads is performed on Luminex carboxy beads, 30 (Luminex, Austin Tex.) at a scale of 50 µl of the standard bead concentration, yielding approximately 650,000 beads. The beads are made of polystyrene, approximately 5.6 µm in diameter, and encoded with controlled amounts of two or three fluorescent dyes to facilitate their bead ID being detected in a purpose-built flow cytometer reading instrument. 50 µl of suspended beads, 30, all of one bead ID or region, are transferred from the Luminex tube in which they are delivered to a 1.5 ml Eppendorf tube for the coupling, 32, with vortexing and sonication used to ensure suspension. The beads are then spun down at 12,000 RPM for 3 minutes and the bead buffer supernatant removed without disturbing the bead pellet. 25 µl of MES buffer is added to each tube of beads, followed by vortexing and sonication. Separately, 10 µg of PCR 2 amplicons, 29, from each BAC are then added to a second set of 1.5 ml centrifuge tubes, and the DNA in each tube is then dried down completely in a SpeedVac (ThermoFisher Scientific, Waltham Mass.). One bead suspension is then transferred into each DNA tube, vortexed and sonicated for 5 seconds each to mix, keeping careful track of the bead ID (region) associated with each BAC.

Next, 1.5 µl of freshly dissolved EDC, 31, (1-ethyl-3-[dimethylaminopropyl]-carbodiimide hypocloride, Pierce, Rockford Ill.) at 10 mg/ml is added to each tube, vortexed immediately, and incubated for 30 minutes at room temperature in the dark (to preserve the Luminex beads' fluorescent encoding). Remixing is performed at the 15-minute point. The EDC addition, incubation, and remixing is then repeated for a second time.

500 µl of TNT buffer (0.1M Tris pH 7.5, 0.15M NaCl, 0.02% Tween 20) is then added to each tube and vortexed. The tubes are then spun on a microfuge for 4 minutes at 12,000 RPM to drive the beads to the bottom and the supernatant carefully removed. Next, 500 µl of 0.1% SDS is added, and the beads again spun down for 4 minutes at 12,000 RPM and the supernatant carefully removed. Finally, 50 µl of 1×TE buffer (10 mM Tris pH 7.5, 1 mM EDTA) to each tube and vortexed.

The bead set, 33, with immobilized amplicon probes, 29, can be included as a component of a multiplex bead set for use in assays of genomic DNA.

Example 2

Preparation of a Multiplex Encoded Bead Set Reagent for DNA Assay

FIG. 2 is a flowchart illustrating mixing in different encoded bead sets, each with its respective immobilized BAC-amplicon probe DNA, together to make a multiplexed encoded bead set.

Encoded bead sets 34, 35, 36, and 37 are forced into suspension by sonication, rotation of a tube container, vortexing or a similar method. A pipette is then used to transfer aliquots of each bead set into another vessel where the individual bead sets are combined and mixed, followed by denaturation, 38, to facilitate subsequent hybridization to the probe DNA immobilized on the beads in an assay.

In a detailed example, the 50 µl contents of 2 or more bead sets, each in an individual tube, each encoded bead set with immobilized probe DNA, 33, are combined in batches into one 1.5 ml centrifuge tube. After combining approximately 10 bead sets, the tube is spun down and the supernatant carefully removed, in order to keep the volume down. This is repeated until all of the bead sets are combined (up to 100 encoded bead IDs or regions are supported by the Luminex 200 system, for example).

After all of the bead sets are combined into a multiplex bead set the immobilized probe DNA is denatured. After spinning down the beads and removing the supernatant, 500 µl 0.1N NaOH is added and allowed to incubate for 2 minutes at room temperature. The beads are then spun down and the supernatant carefully removed. 500 µl of 10 mM Tris, 15 mM NaCL, 0.2% Tween 20 is added, the tube vortexed, then the beads spun down and the supernatant removed. This wash step is then repeated. Finally, the volume is brought to 500 µl with 1×TE buffer, and the multiplex bead set, 39, stored in the dark at 4° C. until used for an assay.

Example 3

Multiplexed Genomic Gain and Loss Assay

Figure 3:
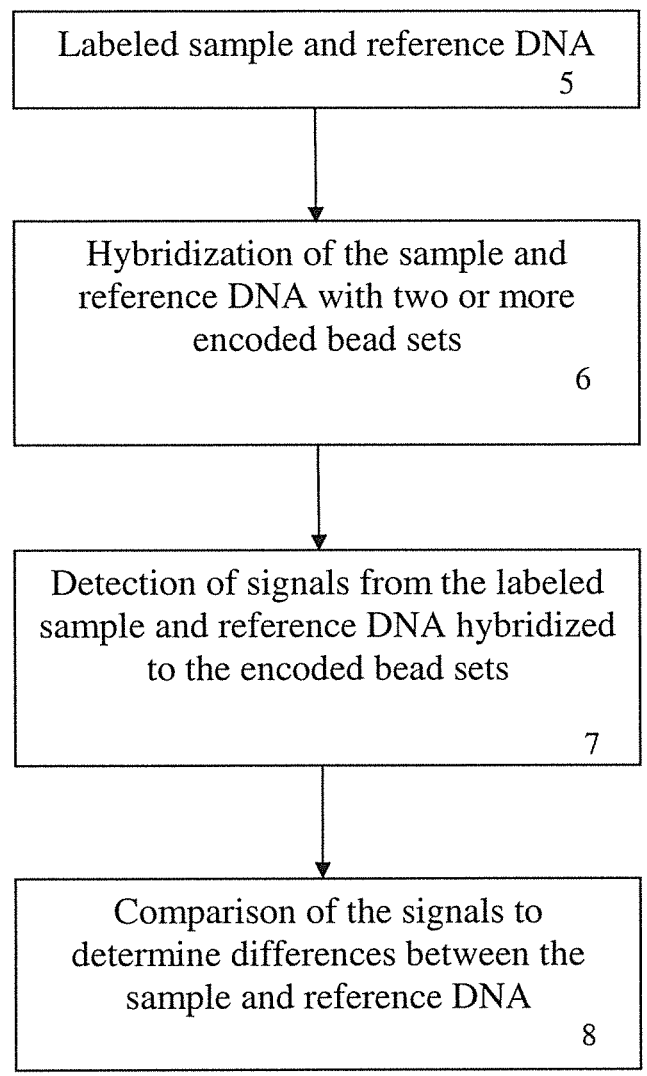
FIG. 3 is a flowchart illustrating an embodiment including running a multiplexed genomic gain and loss assay on n samples using a multiplexed encoded bead set.
Figure 3A:
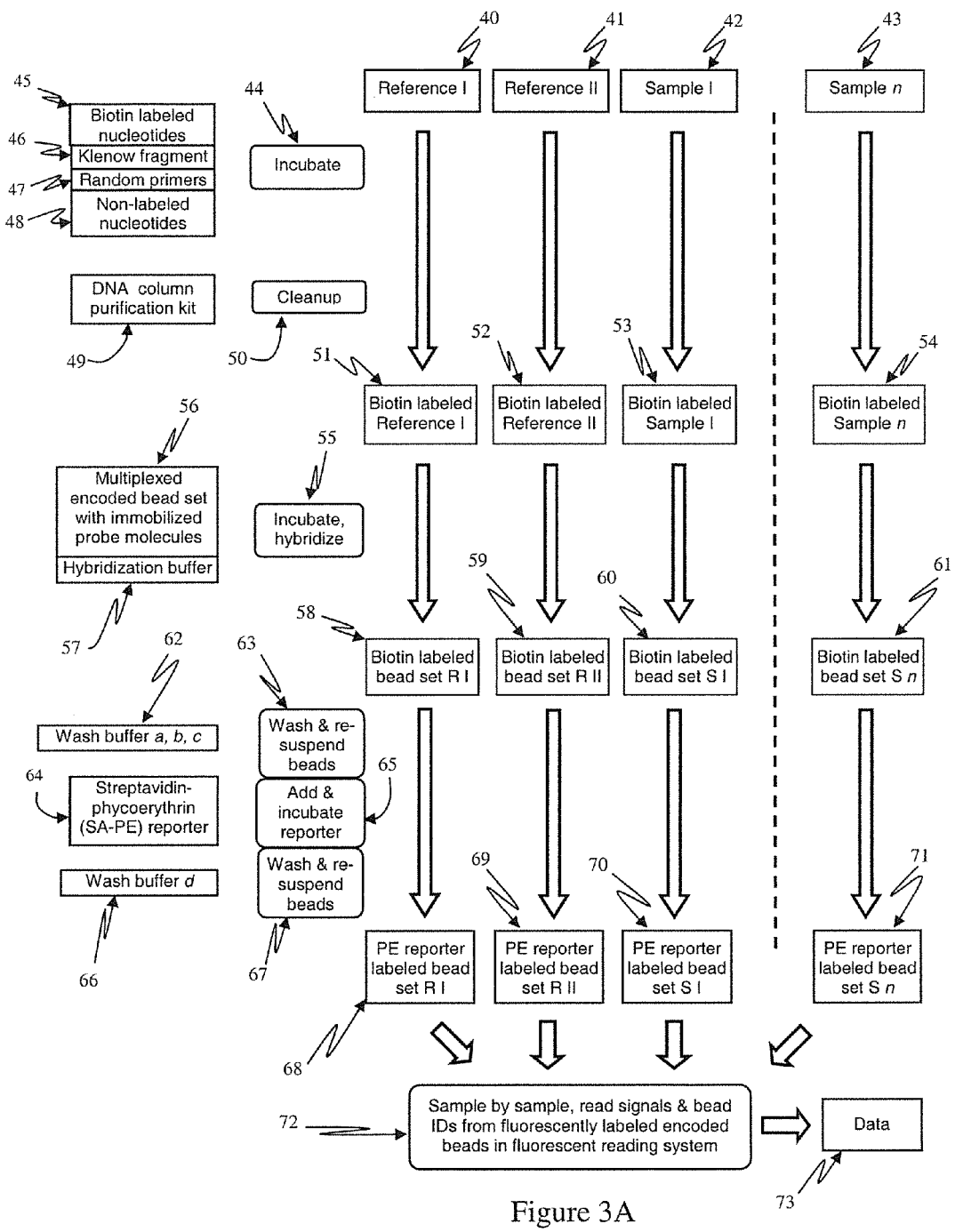
FIG. 3A is a flowchart illustrating an embodiment including running a multiplexed genomic gain and loss assay on n samples using a multiplexed encoded bead set.

FIG. 3A is a flowchart illustrating an embodiment including running a multiplexed genomic gain & loss assay on n samples using a multiplexed encoded bead set.

In this example, two DNA samples and two references are being assayed in parallel. In practice, several dozen samples may be run simultaneously in parallel in a microplate format. More or fewer samples and references than this number can be assayed in parallel.

In this example, the four DNA samples, 40 and 41 representing two references and 42 and 43 representing two assay samples, are enzymatically labeled with biotin and purified. Reference samples are typically normal male and female pooled samples, such as Human Female Genomic DNA and Human Male Genomic DNA (Promega, Madison Wis.). Each DNA sample and reference is combined with biotin-labeled nucleotides, 45, (PerkinElmer, Boston Mass.), non-labeled nucleotides 49, (PerkinElmer), random primers, 47, (Operon, Biotechnologies, Huntsville Ala.) and a Klenow fragment polymerase enzyme, 46 (Epicentre Biotechnologies, Madison Wis.). After incubation, 44, the reaction product is cleaned up, 50, using a DNA column purification kit, 49, such as a Purelink DNA Mini Kit (Invitrogen). Approximately 5 µl at approximately 200 ng/µl of labeled sample is used for subsequent hybridization in the assay.

Each biotin-labeled sample or reference, 51-54, is then hybridized, 55, with the probes immobilized on the beads of a multiplexed encoded bead set, 56. Approximately 500 beads from each bead set (each probe type) are used; in this 55-plex example a total of about 55×500=27,500 beads per hybridization is used.

Beads of each encoded bead set are distinguishable from beads of each of the other encoded bead sets due to the encoding. Each of the 55 bead sets includes a plurality of encoded beads having attached amplicons representing substantially an entire template genomic DNA fragment. The template DNA for each bead set represents a genomic locus listed in FIG. 9.

A hybridization buffer containing Cot-1 DNA, formamide, dextran sulfate and 1.9×SSC is included in the hybridization reaction. The total volume is approximately 15 µl and the reactions are carried out in the wells of a rigid PCR-type microplate, such as the Bio-Rad HSP 9631 (Bio-Rad Laboratories, Hercules Calif.). The plate is sealed tightly to minimize evaporation using an aluminum foil sealer (MSF 1001, Bio-Rad). The hybridization incubation, 55, is performed overnight at 50° C. in a microplate shaking incubator at 1150 rpm (Wallac NCS Incubator, PerkinElmer).

After the hybridization incubation, 55, the four multiplex bead sets hybridized to the four samples, 58-61, are ready for a hybridization wash, 53, followed by incubation with a fluorescent reporter, 65, and a reporter wash, 67. First, 100 µl wash buffer a (2×SSC, 50% formamide) is added to each well, the plate resealed and incubated in the shaking incubator with 1150 rpm agitation at 50° C. for 20 minutes. The contents of each well is then transferred to a Millipore 0.46 µm HT filter plate (Millipore, Billerica Mass.). The liquid is then removed from each well by vacuum using a Millipore MSVMHTS00 vacuum manifold. Next, 100 µl of wash buffer b (2×SSC, 0.1% Igepal detergent) is added to each well, followed by another 20 minute 50° C. shaking incubation and vacuum aspiration. Then, 100 µl of wash buffer c (0.2×SSC) is added to each well and the 20 minute 50° C. shaking incubation is repeated, followed by vacuum aspiration.

100 µl of 1× PhycoLink SA solution, the streptavidin-phycoerythrin reporter, 64, is then added to each well. This reporter solution is made from 2 µl 500× PhycoLink SA PJ13S (Prozyme, San Leandro Calif.) mixed into 1 ml of reporter diluent, where the diluent is 1×PBS, 0.1% BSA and 0.05% Tween 20. This reporter solution is incubated with the multiplex bead sets for 30 minutes at 25° C. and 1050 RPM in the shaking incubator. After incubation, the solution is aspirated from the wells of the filter plate using the vacuum manifold as in the previous wash steps.

The beads are then washed twice, 67, with wash buffer d, 66, which is 1×PBS with 0.01% Tween 20. 100 µl is added to each well of the filter plate, then the liquid is vacuum aspirated through the filters in the bottoms of the plate wells. 100 µl is added a second time and incubated in the shaking incubator for 2 minutes at 25° C. at 1050 RPM. This second wash is not aspirated but used to suspend the beads for reading.

The four bead sets in the example, 68-71, are then ready to read, 72, on a Luminex 200 system (Luminex Corporation, Austin Tex.). The signals and bead IDs from the beads in each well are read in sequence, and the median fluorescence intensity of the first 50 beads of each bead ID (bead region) is recorded for each well or sample, and output in a data file, 73. There is no evidence of bead networking; the Luminex reader is set to analyze 50 beads of each region and no failures are recorded.

Figure 4:
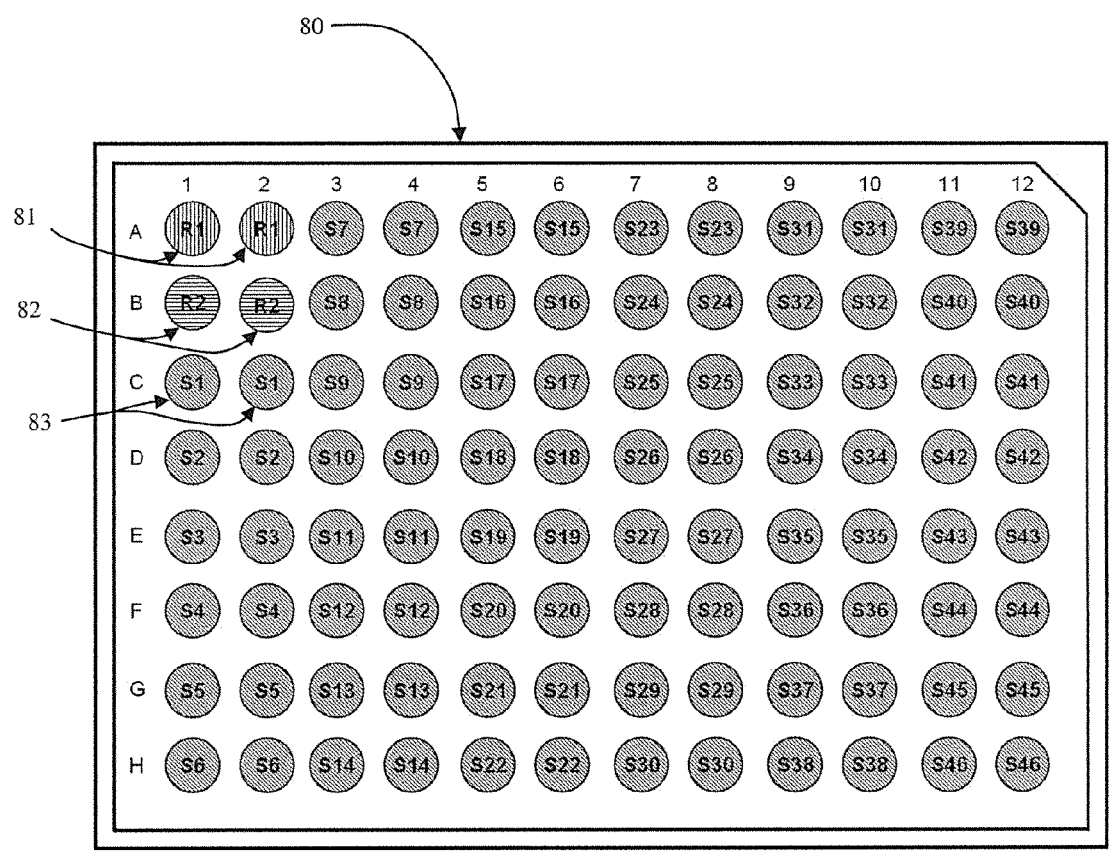
FIG. 4 is a schematic diagram of a 96-well SBS-standard microplate, showing example locations of duplicate references and duplicate samples for running an assay on 46 samples in parallel.

FIG. 4 is a schematic diagram of a 96-well SBS-standard microplate, 80, showing example locations of duplicate references and duplicate samples for running the assay on 46 samples in parallel. Duplicate hybridizations of each labeled sample can be used to assure data generation in case of a well-sealing failure that results in evaporation of the reagents from a single well. When the duplicate is not affected data is still generated from that sample. Using this microplate and encoded bead approach a single laboratory technician can assay, for example, 46 samples and 2 references at a time, all in duplicate, labeling on a first day, hybridizing overnight, and washing and reading on the second day. The assay can alternately be run without replicates or with more than two replicates. Shown are duplicates of two references, 81 and 82, and duplicates of samples, and example of which is indicated at 83.

Figure 5:
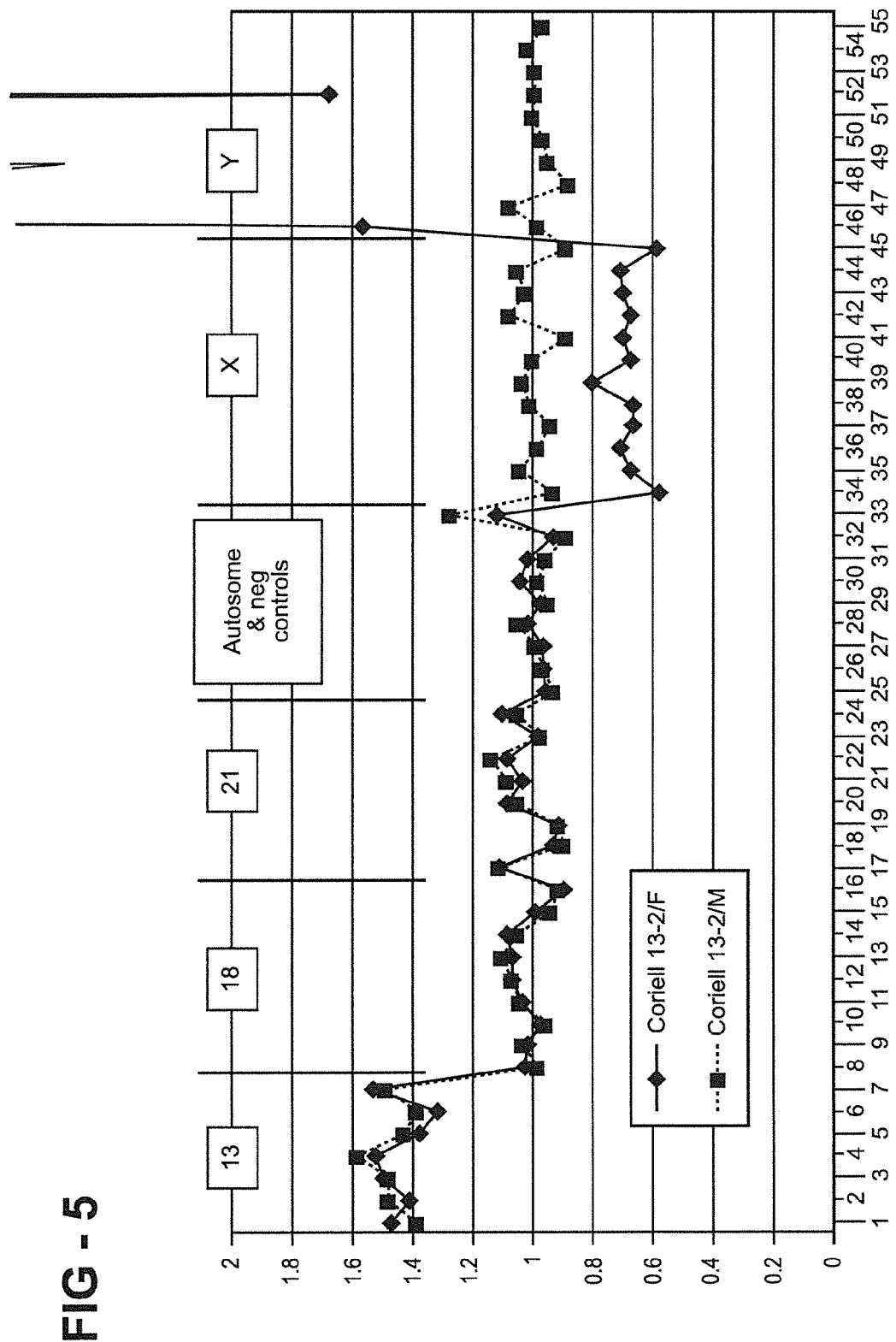
FIG. 5 is an example of data generated using a Coriell DNA sample having a trisomy on chromosome 13, sex male.

FIG. 5 is an example of data generated using a Coriell DNA sample having a trisomy on chromosome 13, sex male. The numbers 1 through 55 shown at the bottom of FIG. 5 are listed in FIG. 9.

This data is calculated from the median fluorescence values for each bead region produced by the Luminex reader. The average values of the negative control beads 29, 54, and 56 are subtracted from all other signals (see FIG. 9). The signals from nine autosomal clones are then ratioed with the corresponding clone signals from the male and female reference DNAs. A normalization factor is calculated such that when the factor is applied to all of the autosomal clone signals it drove the average autosomal ratio to a value of one. This normalization factor is then applied to all of the signals for the sample.

The resulting ratios are plotted and shown in FIG. 5. Note that the ratios for the chromosome 13 clones are all in the range of 1.3 to 1.6, while the clones for chromosomes 18 and 21, as well as the other autosomal clones are but one all below 1.2. The trisomy in chromosome 13 is readily apparent. Also, the ratio plot of the sample compared to male reference (square data points) is effectively flat across the X and Y sex chromosome. This is the response expected from a male sample. The plot of the sample compared to female reference (diamond data points) shifts down for X and up for Y, also as expected for a male sample.

Figure 6:
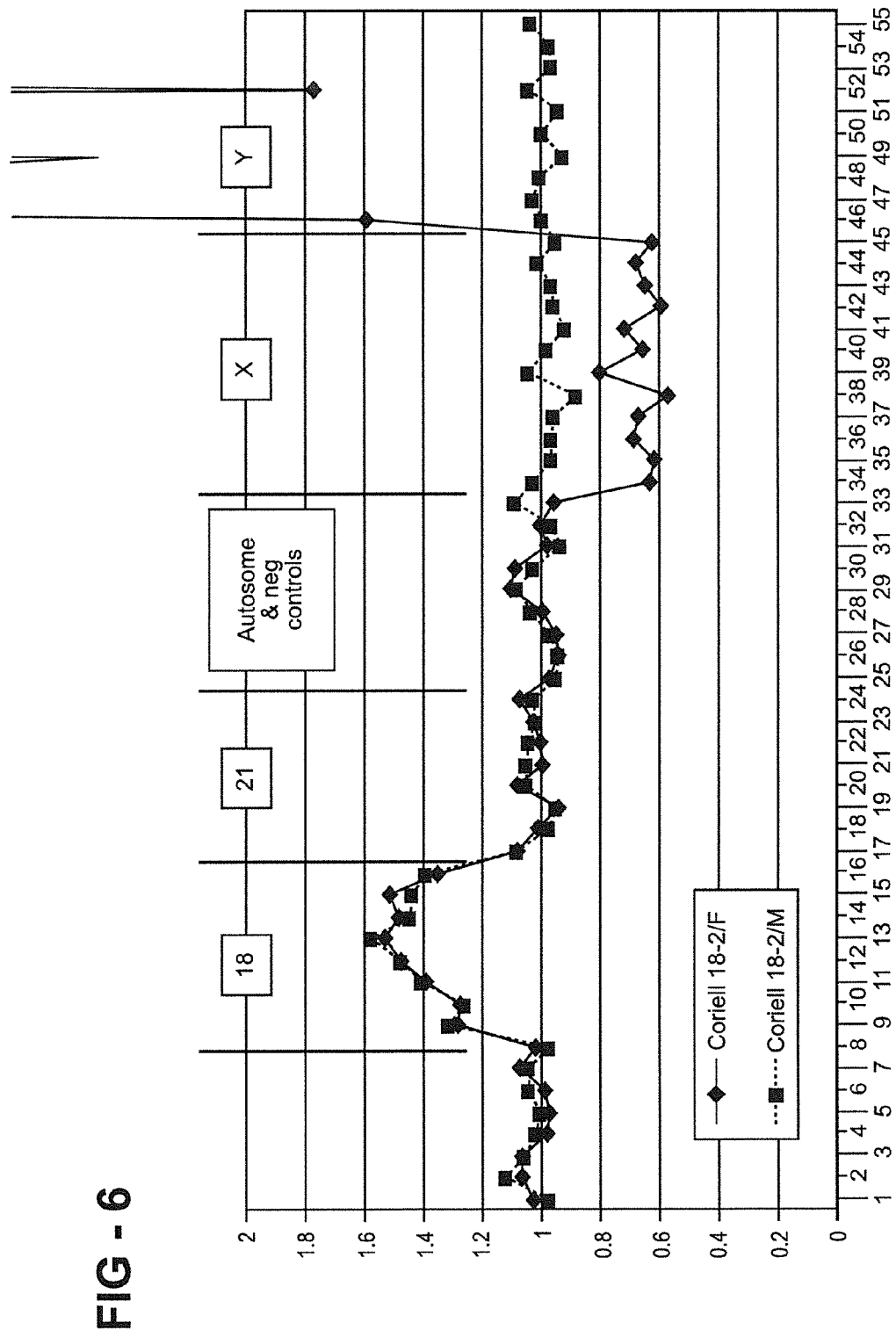
FIG. 6 is an example of data generated using a Coriell DNA sample having a trisomy on chromosome 18, sex male.

FIG. 6 is an example of data generated using a Coriell DNA sample having a trisomy on chromosome 18, sex male. The data is generated and plotted as described for FIG. 5. The numbers 1 through 55 shown at the bottom of FIG. 6 are listed in FIG. 9.

Figure 7:
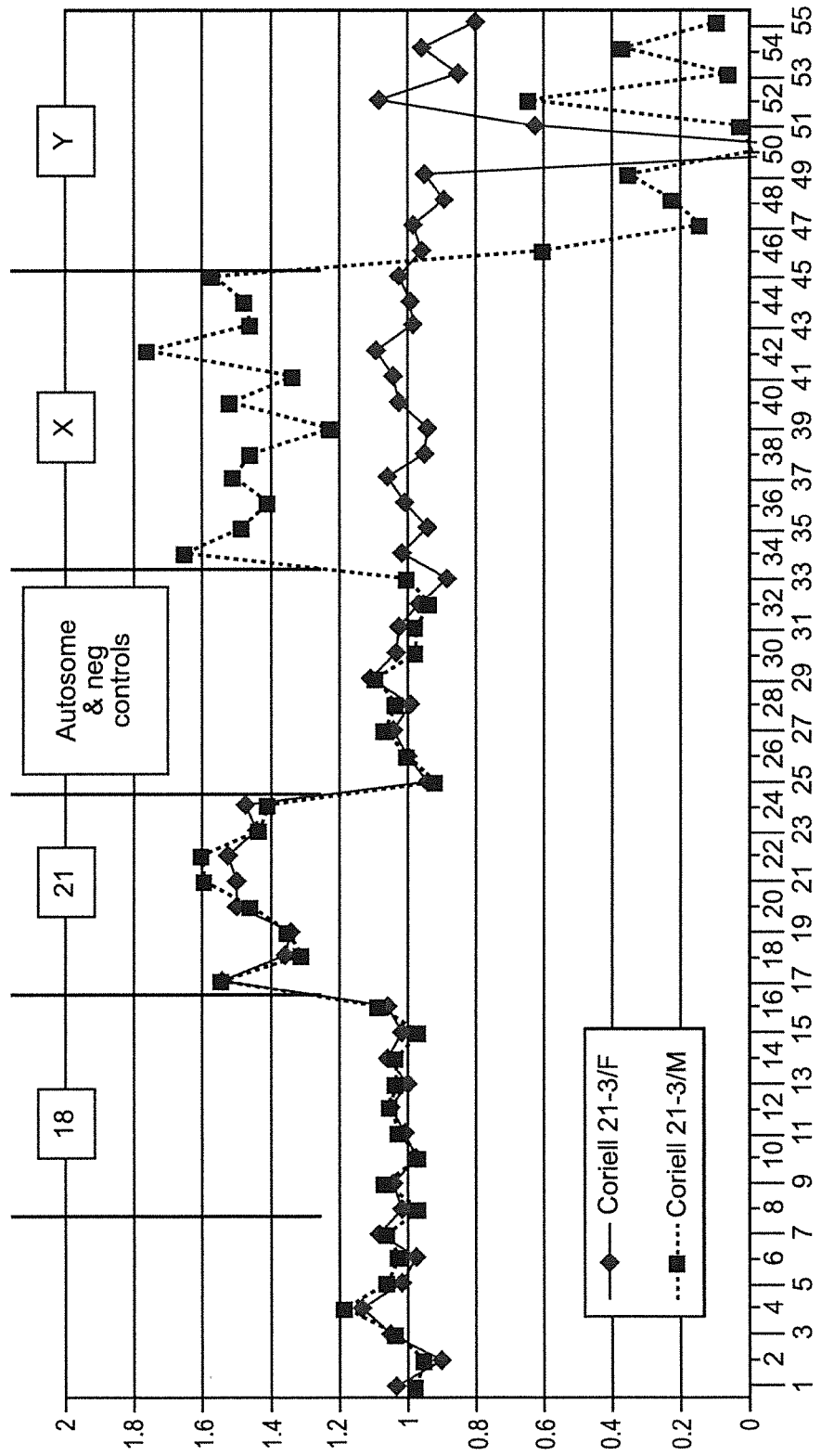
FIG. 7 is an example of data generated using a Coriell DNA sample having a trisomy on chromosome 21, sex female.

FIG. 7 is an example of data generated using a Coriell DNA sample having a trisomy on chromosome 21, sex female. The data is generated and plotted as described for FIG. 5. The numbers 1 through 55 shown at the bottom of FIG. 7 are listed in FIG. 9.

Figure 8:
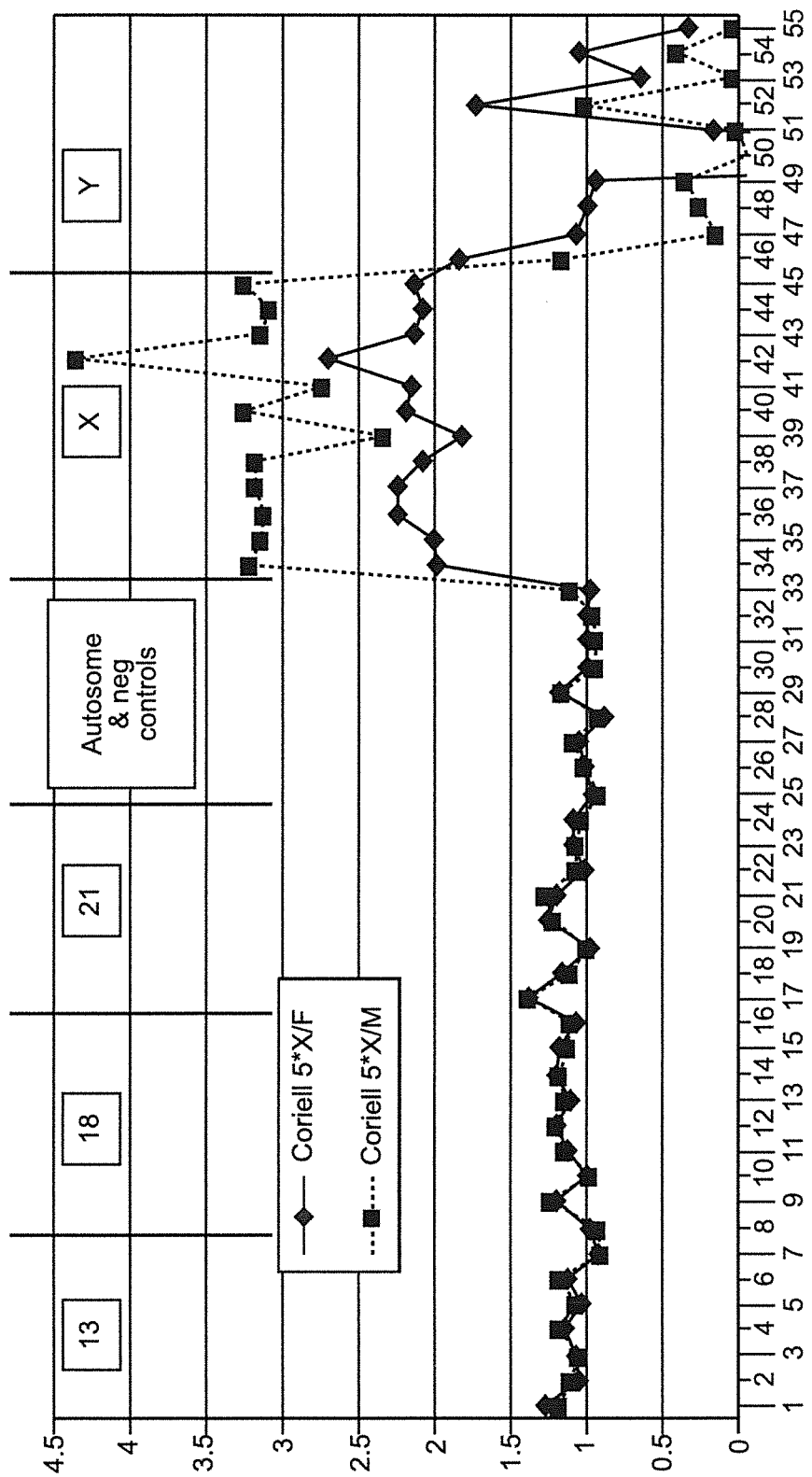
FIG. 8 is an example of data generated using a Coriell DNA sample having a 5-copy amplification of the X chromosome.

FIG. 8 is an example of data generated using a Coriell DNA sample having a 5-copy amplification of the X chromosome. The data is generated and plotted as described for FIG. 5. The numbers 1 through 55 shown at the bottom of FIG. 7 are listed in FIG. 9.

FIG. 9 is a table displaying the BAC clones having human genomic DNA inserts used to generate amplicons in the example assays, their chromosome and cytoband locations, the sequence of the negative control oligonucleotides, and the bead ID (Luminex bead region) for the bead set to which each amplicon probe is immobilized. BAC RP11-186J16 is immobilized to two different bead regions (42 and 86).

For a negative control, an oligonucleotide that has no sequence homology to the human genome is selected. Specific negative control oligonucleotides used are

```
                                               SEQ ID NO. 5
        5' GTCACATGCGATGGATCGAGCTC 3'

SEQ ID NO. 6
        5'CTTTATCATCGTTCCCACCTTAAT 3'

SEQ ID NO. 7
        5'GCACGGACGAGGCCGGTATGTT 3'
```

The signals generated by the three bead regions 29, 54, and 56 having attached negative control oligonucleotides are averaged and subtracted from all other bead signals prior to calculating ratios.

Any patents or publications mentioned in this specification are incorporated herein by reference to the same extent as if each individual publication is specifically and individually indicated to be incorporated by reference. U.S. patent application Ser. No. 11/615,739, filed Dec. 22, 2006 and U.S. Provisional Application Ser. Nos. 60/753,584, filed Dec. 23, 2005, 60/753,822, filed Dec. 23, 2005, 60/765,311, filed Feb. 3, 2006, 60/765,355, filed Feb. 3, 2006 are all incorporated herein by reference in their entirety.

The compositions and methods described herein are presently representative of certain embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A reagent for assaying DNA, comprising:
a plurality of synthetic encoded particles having attached amplicons amplified from a template DNA sequence, wherein each individual synthetic encoded particle of the plurality of synthetic encoded particles comprises multiple different attached amplicons, wherein each individual attached amplicon comprises a DNA sequence identical to a random portion of the template DNA sequence, wherein the attached amplicons together represent substantially the entire template DNA and wherein the DNA sequence identical to a random portion of the template DNA sequence of each individual attached amplicon is shorter than the entire template DNA sequence.

2. The reagent of claim 1, wherein the entire template DNA sequence has a length in the range of about 20-300 kilobases, inclusive and each individual attached amplicon comprises a DNA sequence having a length in the range of about 500-1200 nucleotides, inclusive, which is identical to a random portion of the template DNA sequence.

3. A multiplex reagent for assaying DNA, comprising:
a mixture of two or more pluralities of particles synthetic encoded such that synthetic particles of each plurality of synthetic particles are detectably distinguishable from synthetic particles of each other plurality of synthetic particles, the synthetic encoded particles having attached amplicons amplified from a template DNA sequence, wherein each individual synthetic encoded particle of the two or more pluralities of synthetic encoded particles comprises multiple different attached amplicons, wherein each plurality of synthetic encoded particles having attached amplicons amplified from a different template DNA sequence compared to each other plurality of synthetic encoded particles, each individual attached amplicon comprising a DNA sequence identical to a random portion of the template DNA sequence.

4. A kit for assaying DNA, comprising:
a mixture of two or more pluralities of particles synthetic encoded such that synthetic particles of each plurality of synthetic particles are detectably distinguishable from synthetic particles of each other plurality of synthetic particles, the synthetic encoded particles having attached amplicons amplified from a template DNA sequence, wherein each individual synthetic encoded particle of the two or more pluralities of synthetic encoded particles comprises multiple different attached amplicons, wherein each plurality of synthetic encoded particles having attached amplicons amplified from a different template DNA sequence compared to each other plurality of synthetic encoded particles, each individual attached amplicon comprising a DNA sequence identical to a random portion of the template DNA sequence.

* * * * *